US005580737A

United States Patent [19]
Polisky et al.

[11] Patent Number: 5,580,737
[45] Date of Patent: Dec. 3, 1996

[54] HIGH-AFFINITY NUCLEIC ACID LIGANDS THAT DISCRIMINATE BETWEEN THEOPHYLLINE AND CAFFEINE

[75] Inventors: Barry Polisky; Robert D. Jenison; Larry Gold, all of Boulder, Colo.

[73] Assignee: NeXstar Pharmaceuticals, Inc., Boulder, Colo.

[21] Appl. No.: 443,957

[22] Filed: May 18, 1995

Related U.S. Application Data

[63] Continuation of Ser. No. 134,028, Oct. 7, 1993, abandoned, which is a continuation-in-part of Ser. No. 714,131, Jun. 10, 1991, Pat. No. 5,475,096, and Ser. No. 536,428, Jun. 11, 1990, abandoned.

[51] Int. Cl.$^6$ .................... C07H 21/02; C07H 21/04; C12P 19/34; C12Q 1/68
[52] U.S. Cl. .................... 435/6; 435/91.2; 536/22.1
[58] Field of Search .................... 435/6, 91.2; 536/22.1

[56] References Cited

U.S. PATENT DOCUMENTS

| 5,118,672 | 6/1992 | Schinazi et al. .................... 514/47 |
| 5,270,163 | 12/1993 | Gold et al. . | |

FOREIGN PATENT DOCUMENTS

| 2183661 | 6/1987 | United Kingdom . | |
| WO89/06694 | 7/1989 | WIPO . | |
| WO91/19813 | 12/1991 | WIPO . | |
| WO92/03568 | 3/1992 | WIPO . | |
| 9214843 | 9/1992 | WIPO .................... 435/6 |

OTHER PUBLICATIONS

Tuerk et al., Science 249:505–510(3 Aug. 1990).
Bock et al., Nature 355:564–566(6 Feb. 1992).
Bartel et al. (1991) Cell 67:529.
Bass and Cech (1984) Nature 308:820.
Broussard (1981) Clin. Chem. 27:1931.
Carey et al. (1983) Biochemistry 22:2601.
Ellington (1993) Current Biol. 3:375.
Famulok and Szostak (1992) J. Amer. Chem. Soc. 114:3990.
Gill et al. (1991) J. Mol. Biol. 220:307.
Guschlbauer et al. (1977) Nucleic Acids Res. 4:1933.
Hendeles and Weinberger (1983) Pharmacotherapy 3:2.
Hobbs et al. (1973) Biochem. 12:5138.
Jolly et al. (1981) Clin. Chem. 27:1575.
Joyce (1989) in RNA: Catalysis, Splicing, Evolution, Belfort and Shub (eds.), Elsevier, Amsterdam pp. 83–87.
Kacian et al. (1972) Proc. Natl. Acad. Sci. USA 69:3038.
Kramer et al. (1974) J. Mol. Biol. 89:719.
Levinsohn and Spiegleman (1969) Proc. Natl. Acad. Sci. USA 63:805.
Levinsohn and Spiegleman (1968) Proc. Natl. Acad. Sci. USA 60:866.
Mills et al. (1973) Science 180:916.

(List continued on next page.)

Primary Examiner—Stephanie W. Zitomer
Attorney, Agent, or Firm—Swanson & Bratschun LLC

[57] ABSTRACT

Methods are described for the identification and preparation of nucleic acid ligand ligands to theophylline and caffeine. Included in the invention is a method for identifying nucleic acid ligands with high affinity and selectivity for a target molecule, termed counter-SELEX. One embodiment of counter-SELEX is comprised of the steps of a) preparing a candidate mixture of nucleic acids; b) contacting the candidate mixture with the target, wherein nucleic acids having an increased affinity to the target relative to the candidate mixture may be partitioned form the remainder of the candidate mixture; partitioning the increased affinity nucleic acids from the remainder of the candidate mixture; d) contacting the increased affinity nucleic acids with one or more non-target molecules such that nucleic acid ligands to the non-target molecule(s) are removed; and e) amplifying the nucleic acids with specific affinity to the target molecule to yield a mixture of nucleic acids enriched for nucleic acid sequences with a relatively higher affinity and specificity for binding to the target molecule. Included in the invention are specific nucleic acid ligands to theophylline identified by the method of counter-SELEX.

16 Claims, 11 Drawing Sheets

THEOPHYLLINE

CAFFEINE

OTHER PUBLICATIONS

Mills et al. (1967) Proc. Natl. Acad. Sci. USA 58:217.
Pieken et al. (1991) Science 253:314.
Poncelet et al. Immunoassay 11:77.
Puglisi et al. (1992) Science 257:76.
Romaniuk et al. (1987) Biochemistry 26:1563.
Reinecke et al. (1986) Ann. Emergency Med. 15:147.
Rich et al. (1984) Ann. Rev. Biochem. 53:791.
Riordan et al. (1992) J. Mol. Biol. 226:305.
Robertson and Joyce (1990) NaturE 344:467.
Saffhill et al. (1970) J. Mol. Biol. 51:531.
Schibaharu et al. (1987) Nucleic Acids Res. 15:4403.
Schimmel (1989) Cell 58:9.
Schneider et al. (1992) J. Mol. Biol. Proc. Natl. Acad. Sci. USA 89:6992.
Tao and Frankel (1992) Proc. Natl. Acad. Sci. USA 89:2723.
Tuerk et al. (1992a) Proc. Natl. Acad. Sci. USA 89:6988.
Tuerk et al. (1988) Proc. Natl. Acad. Sci. USA 85:1364.
Tuerk et al. (1992b) in Polymerase Chain Reaction(Ferre et al. eds.) Birkhauser, NY).
Uhlenbeck et al. (1983) J. Biomol. Structure Dynamics 1:539.
Witherell and Uhlenbeck (1989) Biochemistry 28:71.
Yarus (1988) Science 240:1751.
Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kinzler and Vogelstein (1989) Nucleic Acids Research 17:3645.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Thiesen and Bach (1990) Nucleic Acids Research 18:3203.

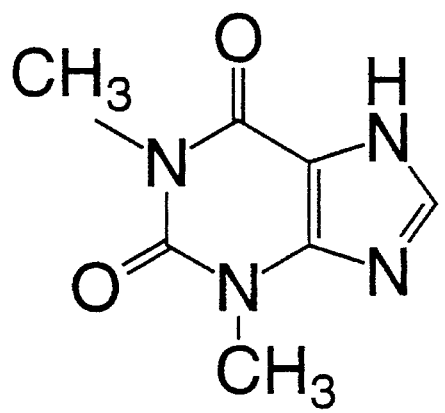 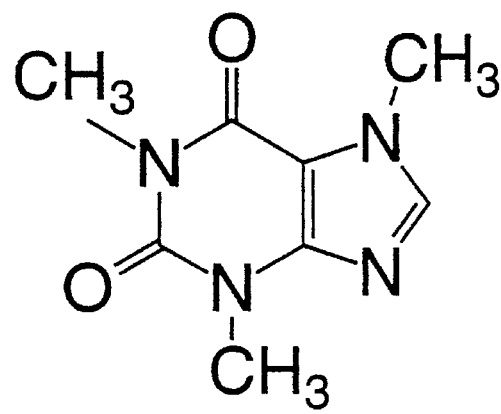
THEOPHYLLINE                         CAFFEINE
FIGURE 1

CLASS I

| | |
|---|---|
| TCT8-6,9 | 5'GAGAAAUACCAGUGACAACUCUCGAGAUCACCCUUGGAAG 3'  SEQ ID NO:3 |
| TCT8-5 | AUACCAUCGUGUAAGCAAGAGACACGACCUUGGCAGUGUG  SEQ ID NO:4 |
| TCT8-1,10 | GAUACCAACAGCAUAU----UUGCUGUCCUUGGAAGCAACGAGA  SEQ ID NO:5 |
| TCT8-4,8 | GUGAUACCAGCAUCGUC----UUGAUGCCCUUGGCAGCACUUCA  SEQ ID NO:6 |
| TCT8-7 | UUGUCGAAUCGGAUACCAGCAAU------GCAGCCCUUGGAAGCAG  SEQ ID NO:7 |
| TR8-14 | GAUACCAACGGCAUAU----UUGCUGUCCUUGGAAGCAACUAUA  SEQ ID NO:8 |
| TR8-8 | CUCUCGAAAUACCAACUACUCUCACA------AUAGUCCUUGGAAG  SEQ ID NO:9 |
| TR8-5 | UUCAUGUCGCUUGAUACCAAUCAACA------AUGACCUUGGAAGCA  SEQ ID NO:10 |

FIGURE 2A

CLASS II

```
TCT8-3   5'UGACUCGAACCCUUGGAAGACCUGAGU------ACAGGUAUACCAG 3'      SEQ ID NO: 11
                                  *          →
TCT8-11           UCCUUGGAAGCCG-------------UACGGAUAUACCAAUUGAGUGGCCAUAUG   SEQ ID NO: 12
                       →
TR8-28   UAUCGAGUGGCCUUGGCAGACCAGGC--------CCGGUAUACCACCA                   SEQ ID NO: 13
                      →
TR8-29   CGAGAUUCAACCUUGGAAGUCAAU---------CGUGAAUACCAUUGUU                  SEQ ID NO: 14
                      →
TR8-9          UCAGAACCUUGGAAGCACUGAAUAAAGAUCAGUUGAUACCA                    SEQ ID NO: 15
                      →
```

TR8-28 (SEQ ID NO:32)

TR8-29 (SEQ ID NO:33)

TCT8-3 (SEQ ID NO:34)

TCT8-11 (SEQ ID NO:35)

```
        N
     N     N          vloop; n=3-12
      N   N
       N N
        NN'
        NN'           vstem 1; nn'=2-6
         C
         C
         U
        AU
        CG    motif 1
        CG
motif 2  A   C/A
        U     A
        A     G
         NN'
         NN'          vstem 2; n=1-8
```

SEQ ID NO: 36

FIGURE 4 mTCT8-4

```
     C
   U   U
    GU
    CG
    UA
    AU
    CG
    GC
     |    C
          C
          U
    AU
    CG
    CG
   A    C
   U    A
   A    G
    GC
    UA
    GC
    GC
   5'   3'
```

(SEQ ID NO: 37)

FIGURE 6

Group 1

| | | | |
|---|---|---|---|
| CR8-16 | GGACGAGACT CATCGTAACC TAGATGGTTG CCAGCATTTA | SEQ ID NO: 16 |
| CR8-18 | GGATGCTTAC AGCATAATCG GAATTGATTG CCAGCGGAAA | SEQ ID NO: 17 |
| CR8-19 | GGGGCAATAG AAGCCAACGC ACAGTCCGTTG CCAGTGTTCG | SEQ ID NO: 18 |
| CR8-21 | GGGATGGATC TTCGGATACG TCAACCAAAG GTTGCCAGCCG | SEQ ID NO: 19 |

Group 2

| | | |
|---|---|---|
| CR8-6,9 | GCGCATCGTA AAAAGGACAA ACGTCGTCGT GACCCCGATA | SEQ ID NO: 20 |
| CR8-12 | GTGCATCGTA AAAAGGACAA ACGTCGTCGT GACCCCGATA | SEQ ID NO: 21 |

Group 3

| | | |
|---|---|---|
| CR8-29 | AGACGGGTGAA ACTGAAATCT AATCCGTCTG AACCCTGGAT | SEQ ID NO: 22 |
| CR8-40 | AGACGGGTGAA GCTGAAATCT AATCCGTCTG AACCCTGGAC | SEQ ID NO: 23 |

Others

| | | |
|---|---|---|
| CR8-34 | GGGAGGTCAA GGACCTCACA CTTTGTGTG CCAGCGCTAT | SEQ ID NO: 24 |
| CR8-37 | GAAAGCCGTTG TGGCCGTGCCA TCGCCCCGCAG GCGAATAACA | SEQ ID NO: 25 |
| CR8-39 | ACGATGGGTT GTTATAGTGG AAACGGTAAG TTCGAGTCTG | SEQ ID NO: 26 |
| CR8-41 | ACGGTGATCC TCTAATCCGT CGACAGAATC GATGTCAATC | SEQ ID NO: 27 |

FIGURE 8

HIGH-AFFINITY NUCLEIC ACID LIGANDS THAT DISCRIMINATE BETWEEN THEOPHYLLINE AND CAFFEINE

This application is a Continuation of U.S. patent application Ser. No. 08/134,028, filed Oct. 7, 1993, now abandoned, which is a Continuation-in-Part of U.S. patent application Ser. No. 07/714,131, filed Jun. 10, 1991, entitled Nucleic Acid Ligands, now issued as U.S. Pat. No. 5,475,096, and U.S. patent application Ser. No. 07/536,428, filed Jun. 11, 1990, entitled Systematic Evolution of Ligands by Exponential Enrichment, now abandoned.

FIELD OF THE INVENTION

Described herein are high affinity nucleic acid ligands to theophylline and caffeine. The method utilized herein for identifying such nucleic acid ligands is called SELEX, an acronym for Systematic Evolution of Ligands by EXponential enrichment. Further described herein are methods for identifying highly specific nucleic acid ligands able to discriminate between closely related molecules, termed "counter-SELEX". Specifically disclosed herein are high-affinity RNA ligands able to discriminate between theophylline and caffeine. Further included within the scope of this invention are modified nucleic acid ligands and mimetic ligands that are informed by the nucleic acid ligands identified herein.

BACKGROUND OF THE INVENTION

Most proteins or small molecules are not known to specifically bind to nucleic acids. The known protein exceptions are those regulatory proteins such as repressors, polymerases, activators and the like which function in a living cell to bring about the transfer of genetic information encoded in the nucleic acids into cellular structures and the replication of the genetic material. Furthermore, small molecules such as GTP bind to some intron RNAs.

Living matter has evolved to limit the function of nucleic acids to a largely informational role. The Central Dogma, as postulated by Crick, both originally and in expanded form, proposes that nucleic acids (either RNA or DNA) can serve as templates for the synthesis of other nucleic acids through replicative processes that "read" the information in a template nucleic acid and thus yield complementary nucleic acids. All of the experimental paradigms for genetics and gene expression depend on these properties of nucleic acids: in essence, double-stranded nucleic acids are informationally redundant because of the chemical concept of base pairs and because replicative processes are able to use that base pairing in a relatively error-free manner.

The individual components of proteins, the twenty natural amino acids, possess sufficient chemical differences and activities to provide an enormous breadth of activities for both binding and catalysis. Nucleic acids, however, are thought to have narrower chemical possibilities than proteins, but to have an informational role that allows genetic information to be passed from virus to virus, cell to cell, and organism to organism. In this context nucleic acid components, the nucleotides, possess only pairs of surfaces that allow informational redundancy within a Watson-Crick base pair. Nucleic acid components need not possess chemical differences and activities sufficient for either a wide range of binding or catalysis.

However, some nucleic acids found in nature do participate in binding to certain target molecules and even a few instances of catalysis have been reported. The range of activities of this kind is narrow compared to proteins and more specifically antibodies. For example, where nucleic acids are known to bind to some protein targets with high affinity and specificity, the binding depends on the exact sequences of nucleotides that comprise the DNA or RNA ligand. Thus, short double-stranded DNA sequences are known to bind to target proteins that repress or activate transcription in both prokaryotes and eukaryotes. Other short double-stranded DNA sequences are known to bind to restriction endonucleases, protein targets that can be selected with high affinity and specificity. Other short DNA sequences serve as centromeres and telomeres on chromosomes, presumably by creating ligands for the binding of specific proteins that participate in chromosome mechanics. Thus, double-stranded DNA has a well-known capacity to bind within the nooks and crannies of target proteins whose functions are directed to DNA binding. Single-stranded DNA can also bind to some proteins with high affinity and specificity, although the number of examples is rather smaller. From the known examples of double-stranded DNA binding proteins, it has become possible to describe some of the binding interactions as involving various protein motifs projecting amino acid side chains into the major groove of B form double-stranded DNA, providing the sequence inspection that allows specificity.

Double-stranded RNA occasionally serves as a ligand for certain proteins, for example, the endonuclease RNase III from *E. coli*. There are more known instances of target proteins that bind to single-stranded RNA ligands, although in these cases the single-stranded RNA often forms a complex three-dimensional shape that includes local regions of intramolecular double-strandedness. The amino acyl tRNA synthetases bind tightly to tRNA molecules with high specificity. A short region within the genomes of RNA viruses binds tightly and with high specificity to the viral coat proteins. A short sequence of RNA binds to the bacteriophage T4-encoded DNA polymerase, again with high affinity and specificity. Thus, it is possible to find RNA and DNA ligands, either double- or single-stranded, serving as binding partners for specific protein targets. Most known DNA binding proteins bind specifically to double-stranded DNA, while most RNA binding proteins recognize single-stranded RNA. This statistical bias in the literature no doubt reflects the present biosphere's statistical predisposition to use DNA as a double-stranded genome and RNA as a single-stranded entity in the roles RNA plays beyond serving as a genome. Chemically there is no strong reason to dismiss single-stranded DNA as a fully able partner for specific protein interactions.

RNA and DNA have also been found to bind to smaller target molecules. Double-stranded DNA binds to various antibiotics, such as actinomycin D. A specific single-stranded RNA binds to the antibiotic thiostreptone; specific RNA sequences and structures probably bind to certain other antibiotics, especially those whose function is to inactivate ribosomes in a target organism. A family of evolutionary related RNAs binds with specificity and decent affinity to nucleotides and nucleosides (Bass, B. and Cech, T. (1984) Nature 308:820–826) as well as to one of the twenty amino acids (Yarus, M. (1988) Science 240:1751–1758). Catalytic RNAs are now known as well, although these molecules perform over a narrow range of chemical possibilities, which are thus far related largely to phosphodiester transfer reactions and hydrolysis of nucleic acids.

Despite these known instances, the great majority of proteins and other cellular components are thought not to bind to nucleic acids under physiological conditions and such binding as may be observed is non-specific. Either the capacity of nucleic acids to bind other compounds is limited to the relatively few instances enumerated supra, or the chemical repertoire of the nucleic acids for specific binding is avoided (selected against) in the structures that occur naturally. The present invention is premised on the inventors' fundamental insight that nucleic acids as chemical compounds can form a virtually limitless array of shapes, sizes and configurations, and are capable of a far broader repertoire of binding and catalytic functions than those displayed in biological systems.

The chemical interactions have been explored in cases of certain known instances of protein-nucleic acid binding. For example, the size and sequence of the RNA site of bacteriophage R17 coat protein binding has been identified by Uhlenbeck and coworkers. The minimal natural RNA binding site (21 bases long) for the R17 coat protein was determined by subjecting variable-sized labeled fragments of the mRNA to nitrocellulose filter binding assays in which protein-RNA fragment complexes remain bound to the filter (Carey et al. (1983) Biochemistry 22:2601). A number of sequence variants of the minimal R17 coat protein binding site were created in vitro in order to determine the contributions of individual nucleic acids to protein binding (Uhlenbeck et a 1. (1983) J. Biomol. Structure Dynamics 1:539 and Romaniuk et al. (1987) Biochemistry 26:1563). It was found that the maintenance of the hairpin loop structure of the binding site was essential for protein binding but, in addition, that nucleotide substitutions at most of the single-stranded residues in the binding site, including a bulged nucleotide in the hairpin stem, significantly affected binding. In similar studies, the binding of bacteriophage Qβ coat protein to its translational operator was examined (Witherell and Uhlenbeck (1989) Biochemistry 28:71). The Qβ coat protein RNA binding site was found to be similar to that of R17 in size, and in predicted secondary structure, in that it comprised about 20 bases with an 8 base pair hairpin structure which included a bulged nucleotide and a 3 base loop. In contrast to the R17 coat protein binding site, only one of the single-stranded residues of the loop is essential for binding and the presence of the bulged nucleotide is not required. The protein-RNA binding interactions involved in translational regulation display significant specificity.

Nucleic acids are known to form secondary and tertiary structures in solution. The double-stranded forms of DNA include the so-called B double-helical form, Z-DNA and superhelical twists (Rich, A. et al. (1984) Ann. Rev. Biochem. 53:791–846). Single-stranded RNA forms localized regions of secondary structure such as hairpin loops and pseudoknot structures (Schimmel, P. (1989) Cell 58:9–12). However, little is known concerning the effects of unpaired loop nucleotides on stability of loop structure, kinetics of formation and denaturation, thermodynamics, and almost nothing is known of tertiary structures and three dimensional shape, nor of the kinetics and thermodynamics of tertiary folding in nucleic acids (Tuerk, C. et al. (1988) Proc. Natl. Acad. Sci. USA 85:1364–1368).

A type of in vitro evolution was reported in replication of the RNA bacteriophage Qβ. Mills, D. R. et al. (1967) Proc. Natl. Acad. Sci USA 58:217–224; Levinsohn, R. and Spiegleman, S. (1968) Proc. Natl. Acad. Sci. USA 60:866–872; Levinsohn, R. and Spiegleman S. (1969) Proc. Natl. Acad. Sci. USA 63:805–811; Saffhill, R. et al. (1970) J. Mol. Biol. 51:531–539; Kacian, D. L. et al. (1972) Proc. Natl. Acad. Sci. USA 69:3038–3042; Mills, D. R. et al. (1973) Science 180:916–927. The phage RNA serves as a poly-cistronic messenger RNA directing translation of phage-specific proteins and also as a template for its own replication catalyzed by Qβ RNA replicase. This RNA replicase was shown to be highly specific for its own RNA templates. During the course of cycles of replication in vitro small variant RNAs were isolated which were also replicated by Qβ replicase. Minor alterations in the conditions under which cycles of replication were performed were found to result in the accumulation of different RNAs, presumably because their replication was favored under the altered conditions. In these experiments, the selected RNA had to be bound efficiently by the replicase to initiate replication and had to serve as a kinetically favored template during elongation of RNA. Kramer et al. (1974) J. Mol. Biol. 89:719 reported the isolation of a mutant RNA template of Qβ replicase, the replication of which was more resistant to inhibition by ethidium bromide than the natural template. It was suggested that this mutant was not present in the initial RNA population but was generated by sequential mutation during cycles of in vitro replication with Qβ replicase. The only source of variation during selection was the intrinsic error rate during elongation by Qβ replicase. In these studies what was termed "selection" occurred by preferential amplification of one or more of a limited number of spontaneous variants of an initially homogenous RNA sequence. There was no selection of a desired result, only that which was intrinsic to the mode of action of Qβ replicase.

Joyce and Robertson (Joyce (1989) in *RNA: Catalysis, Splicing, Evolution*, Belfort and Shub (eds.), Elsevier, Amsterdam pp. 83–87; and Robertson and Joyce (1990) Nature 344:467) reported a method for identifying RNAs which specifically cleave single-stranded DNA. The selection for catalytic activity was based on the ability of the ribozyme to catalyze the cleavage of a substrate ssRNA or DNA at a specific position and transfer the 3'-end of the substrate to the 3'-end of the ribozyme. The product of the desired reaction was selected by using a deoxyoligonucleotide primer which could bind only to the completed product across the junction formed by the catalytic reaction and allowed selective reverse transcription of the ribozyme sequence. The selected catalytic sequences were amplified by attachment of the promoter of T7 RNA polymerase to the 3'-end of the cDNA, followed by transcription to RNA. The method was employed to identify from a small number of ribozyme variants the variant that was most reactive for cleavage of a selected substrate.

The prior art has not taught or suggested more than a limited range of chemical functions for nucleic acids in their interactions with other substances: as targets for proteins that had evolved to bind certain specific oligonucleotide sequences; and more recently, as catalysts with a limited range of activities. Prior "selection" experiments have been limited to a narrow range of variants of a previously described function. Now, for the first time, it will be understood that the nucleic acids are capable of a vastly broad range of functions and the methodology for realizing that capability is disclosed herein.

U.S. patent application Ser. No. 07/536,428 filed Jun. 11, 1990, of Gold and Tuerk, entitled Systematic Evolution of Ligands by Exponential Enrichment, U.S. patent application Ser. No. 07/714,131 filed Jun. 10, 1992 of Gold and Tuerk, U.S. patent application Ser. No. 07/931,473, filed Aug. 17, 1992, of Gold and Tuerk, issued as U.S. Pat. No. 5,270,163, both entitled Nucleic Acid Ligands (See also PCT/US91/04078) describe a fundamentally novel method for making a nucleic acid ligand for any desired target. Each of these applications, collectively referred to herein as the SELEX Patent Applications, is specifically incorporated herein by reference.

The method of the SELEX Patent Applications is based on the unique insight that nucleic acids have sufficient capacity for forming a variety of two- and three-dimensional structures and sufficient chemical versatility available within their monomers to act as ligands (form specific binding pairs) with virtually any chemical compound, whether large or small in size.

The method involves selection from a mixture of candidates and step-wise iterations of structural improvement, using the same general selection theme, to achieve virtually any desired criterion of binding affinity and selectivity. Starting from a mixture of nucleic acids, preferably comprising a segment of randomized sequence, the method, termed SELEX herein, includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

While not bound by theory, SELEX is based on the inventors' insight that within a nucleic acid mixture containing a large number of possible sequences and structures there is a wide range of binding affinities for a given target. A nucleic acid mixture comprising, for example a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations.

In one embodiment of the method of the SELEX Patent Applications, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX procedures with contiguous randomized segments be initiated with nucleic acid sequences containing a randomized segment of between about 20–50 nucleotides.

The SELEX Patent Applications also describe methods for obtaining nucleic acid ligands that bind to more than one site on the target molecule, and to nucleic acid ligands that include non-nucleic acid species that bind to specific sites on the target. The SELEX method provides means for isolating and identifying nucleic acid ligands which bind to any envisionable target. However, in preferred embodiments the SELEX method is applied to situations where the target is a protein, including both nucleic acid-binding proteins and proteins not known to bind nucleic acids as part of their biological function.

Theophylline (1,3-dimethylxanthine)(FIG. 1) is a naturally occurring alkaloid that is widely used as an effective bronchodilator in the treatment of asthma, bronchitis, and emphysema (Hendeles and Weinberger (1983) Pharmacotherapy 3:2). Because of its narrow therapeutic index, serum levels must be monitored carefully to avoid serious toxicity. Theophylline is closely related structurally to caffeine (1,3, 7-trimethylxanthine)(FIG. 1) and theobromine (3,7-dimethylxanthine), both of which are often present in serum samples; analytical diagnostic techniques utilizing spectroscopic characteristics or immunological reagents must therefore discriminate efficiently among these and other alkaloids (Jolley et al. (1981) Clin. Chem. 27:1575; Broussard (1981) Clin. Chem. 27:1931; Reinecke et al. (1986) Ann. Emergency Med. 15:147).

SUMMARY OF THE INVENTION

The present invention includes methods for identifying and producing nucleic acid ligands of theophylline and caffeine, and the nucleic acid ligands so identified and produced.

Nucleic acid sequences identified through the SELEX process are provided that are ligands of theophylline. Specifically, RNA sequences are provided that are capable of binding with high affinity to theophylline. Included within the invention are the nucleic acid ligand sequences shown in FIGS. 2A and 2B (TR8 and TCT8). Also included are RNA ligands to theophylline identified through the SELEX method that are substantially homologous to those shown in FIGS. 2A and 2B and that have substantially the same ability to bind theophylline. Further included in this invention are RNA ligands to theophylline that have substantially the same structural form as the SELEX identified ligands shown in FIGS. 2A and 2B and that have substantially the same ability to bind theophylline.

Nucleic acid sequences identified through the SELEX process are provided that are ligands of caffeine. Specifically, RNA sequences are provided that are capable of binding with high affinity to caffeine. Included within the invention are the nucleic acid ligand sequences shown in FIG. 8 (CR8). Also included are RNA ligands to caffeine identified through the SELEX method that are substantially homologous to those shown in FIG. 8 and that have substantially the same ability to bind caffeine. Further included in this invention are RNA ligands to caffeine that have substantially the same structural form as the SELEX identified ligands shown in FIG. 8 and that have substantially the same ability to bind caffeine.

Included in this invention is an extension of the SELEX method of identifying nucleic acid ligands, termed counter-SELEX. Counter-SELEX is a method for improving the specificity of nucleic acid ligands to a target molecule by eliminating nucleic acid ligand sequences with cross-reactivity to one or more non-target molecules. Counter-SELEX is comprised of the steps of a) preparing a candidate mixture of nucleic acids; b) contacting the candidate mixture with the target, wherein nucleic acids having an increased affinity to the target relative to the candidate mixture may be partitioned from the remainder of the candidate mixture; c) partitioning the increased affinity nucleic acids from the remainder of the candidate mixture; d) contacting the increased affinity nucleic acids with one or more non-target molecules such that nucleic acid ligands with specific affinity for the non-target molecule(s) are removed; and e) amplifying the nucleic acids with specific affinity to the target molecule to yield a mixture of nucleic acids enriched for nucleic acid sequences with a relatively higher affinity and specificity for binding to the target molecule.

The present invention includes the nucleic acid ligands to theophylline identified according to the above-described counter-SELEX method, including those ligands listed in FIG. 2 (TCT8). Also included are nucleic acid ligands to theophylline that are substantially homologous to any of the given ligands and that have substantially the same ability to bind theophylline. Further included in this invention are nucleic acid ligands to theophylline that have substantially the same structural form as the ligands presented herein and that have substantially the same ability to bind theophylline.

The present invention further includes the nucleic acid ligands to caffeine identified according to the SELEX method.

The SELEX Patent Applications disclose nucleic acid ligands that have been modified at the ribose and/or phosphate and/or base positions to increase in vivo stability of the RNA ligand. The present invention also includes modified nucleotide sequences based on the nucleic acid ligand sequences identified herein and mixtures of the same. Other modifications to RNA ligands are encompassed by this invention, including specific alterations in base sequence, and additions of nucleic acids or non-nucleic acid moieties to the original compound. Specifically included in the present invention are the nucleic acid ligands of theophylline shown in FIG. 2 with one or more 2'-amino (2'-NH$_2$), 2'-fluoro (2'-F) and/or 2'-Omethyl (2'-OMe) modified nucleotides. Further included in the invention are the nucleic acid ligands of caffeine shown in FIG. 8 with one or more 2'-NH$_2$, 2'-F and/or 2'-OMe modified nucleotides.

BRIEF DESCRIPTION OF THE FIGURES

FIG. 1 shows the structures of theophylline and caffeine.

FIG. 2 shows the aligned sequences for two classes of RNA molecules with affinity for theophylline selected through the SELEX method (designated TR8) and counter-SELEX method (designated TCT8). FIG. 2A shows the Class I sequences, FIG. 2B shows the Class II sequences. The clone number from which the sequence was derived is shown at the left of the sequence. In some cases, multiple isolates were obtained. Sequences shown comprised the 40 nucleotide sequence that was initially random at the start of the SELEX process. The bold uppercase sequence is conserved and provides the basis for the alignment. The arrows overlay regions of potential intramolecular base complementarity. The asterisk marks the single position in motif 1 that shows variability. Dashes represent absence of a nucleotide. Class I and II are related by circular permutation.

FIGS. 3A and 3B illustrate the predicted secondary structures for theophylline binding RNA species obtained from the TR8 SELEX and TCT8 SELEX experiments. Bases in shadow text were initially present in either the fixed 5' or 3' regions which flanked the random region. Note that either fixed region can contribute to the proposed structure. The arrows in the TCT8-4 ligand represent the termini of the mini-derivative mTCT8-4 with the exception that the position 1-38 AU pair was changed to a GC pair in mTCT8-4.

FIG. 4 illustrates the predicted secondary structure of theophylline binding RNA species. N and N' are any complementary base pair. Numbers represent the size range of the various domains observed in the ligands obtained.

FIG. 6 shows the predicted secondary structure for mTCT8-4.

FIG. 8 shows the sequences of RNA ligands for caffeine (CR8). These ligands were identified after 8 SELEX selection rounds.

DETAILED DESCRIPTION OF THE PREFERRED EMBODIMENTS

Figure 3A:
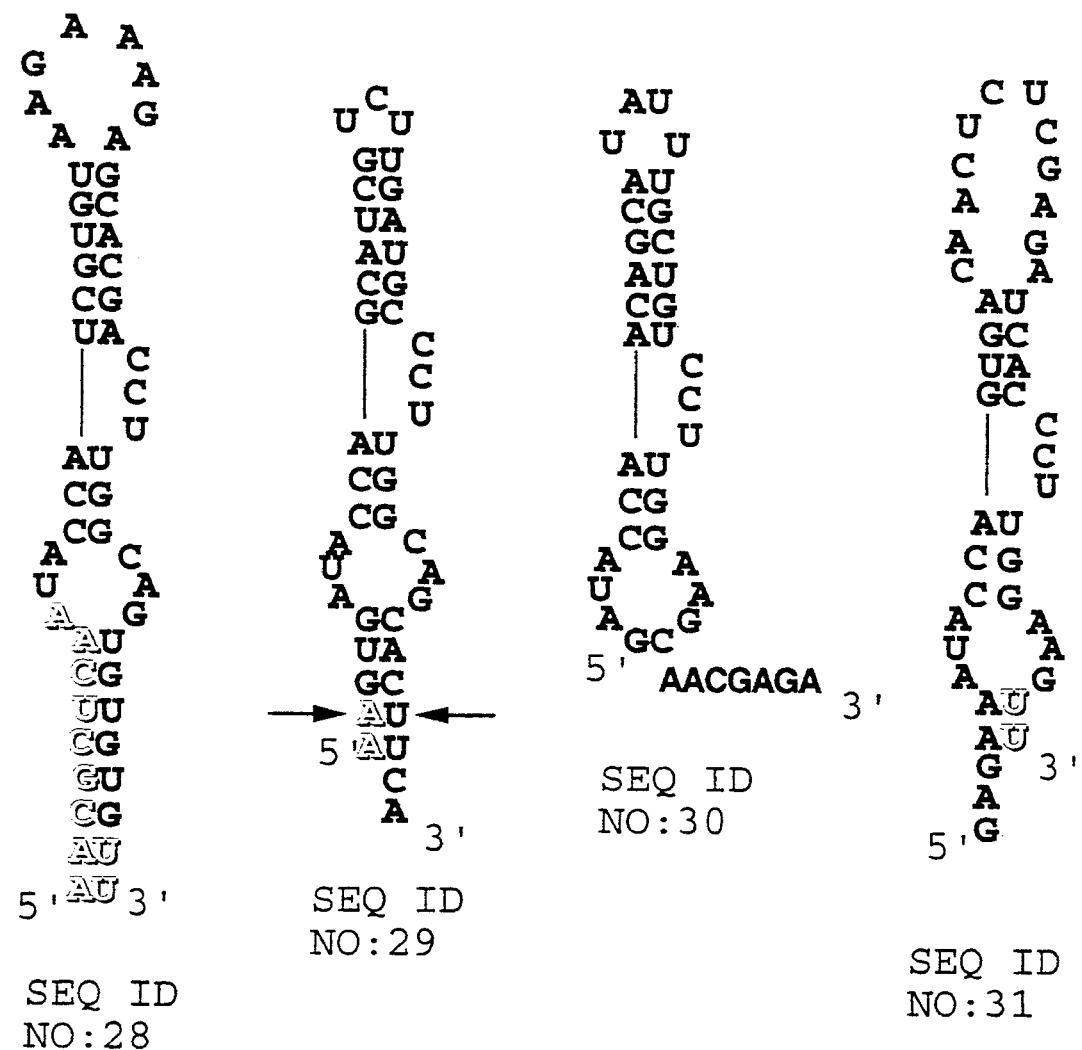

This application is an extension and an improvement of the method for identifying nucleic acid ligands referred to as SELEX. The SELEX method is described in detail in U.S. patent application Ser. No. 07/931,473, filed Aug. 17, 1992, issued as U.S. Pat. No. 5,270,163,. U.S. patent application Ser. No. 07/714,131 filed Jun. 10, 1991 entitled Nucleic Acid Ligands and Ser. No. 07/536,428 filed Jun. 11, 1990 entitled Systematic Evolution of Ligands by EXponential Enrichment. The full text of these applications, including but not limited to, all definitions and descriptions of the SELEX process, are specifically incorporated herein by reference.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets wherein the protein is and is not a nucleic acid binding protein.

SELEX provides high affinity ligands of a target molecule. This represents a singular achievement that is unprecedented in the field of nucleic acids research. The present invention applies the SELEX procedure to the specific targets of theophylline and caffeine. In the Example section below, the experimental parameters used to isolate and identify the nucleic acid ligand solutions to theophylline are described.

In order to produce nucleic acids desirable for use as a pharmaceutical, it is preferred that the nucleic acid ligand 1) binds to the target in a manner capable of achieving the desired effect on the target; 2) be as small as possible to obtain the desired effect; 3) be as stable as possible; and 4) be a specific ligand to the chosen target. In most, if not all, situations it is preferred that the nucleic acid ligand have the highest possible affinity to the target.

In co-pending and commonly assigned U.S. patent application Ser. No. 07/964,624, filed Oct. 21, 1992 ('624), methods are described for obtaining improved nucleic acid ligands after SELEX has been performed. This application, entitled Methods of Producing Nucleic Acid Ligands is specifically incorporated herein by reference. Included in the '624 application are the following methods relating to: Assays of ligand effects on target molecules; Affinity assays of the ligands; Information boundaries determination; Quantitative and qualitative assessment of individual nucleotide contributions to affinity via secondary SELEX, nucleotide substitution, and chemical modification experiments; and Structural determination. The present invention includes improvements to the nucleic acid ligand solution derived according to these procedures.

This invention includes the specific nucleic acid ligands of theophylline shown in FIGS. 2A and 2B. The scope of the ligands covered by this invention extends to all ligands of theophylline identified according to the SELEX procedure and the counter-SELEX procedure. More specifically, this invention includes nucleic acid sequences that are substantially homologous to and that have substantially the same ability to bind theophylline as the specific nucleic acid ligands shown in FIGS. 2A and 2B. By substantially homologous, it is meant, a degree of primary sequence homology in excess of 70%, most preferably in excess of 80%. Substantially the same ability to bind theophylline means that the affinity is within two orders of magnitude, and preferably within one order of magnitude, of the affinity of the ligands described herein. It is well within the skill of those of ordinary skill in the art to determine whether a given sequence—substantially homologous to those specifically described herein—has substantially the same ability to bind theophylline.

A review of the proposed structural formations shown in FIG. 2A for the Class I and FIG. 2B for the Class II ligands of theophylline shows that sequences that have little or no primary sequence homology may still have substantially the same ability to bind theophylline. It can be assumed that the disparate sequences may have similar structures that give rise to the ability to bind to theophylline, and that each of the Class I and Class II sequence ligands are able to assume structures that contain essentially identical theophylline binding sites. For these reasons, the present invention also includes nucleic acid ligands that have substantially the same structure as the ligands presented herein and that have substantially the same ability to bind theophylline as the nucleic acid ligands shown in FIGS. 2A and 2B. "Substantially the same structure" includes all RNA ligands having the common structural elements of the sequences given in FIGS 2A and 2B.

This invention includes the specific nucleic acid ligands of caffeine shown in FIG. 8. The scope of the ligands covered by this invention extends to all ligands of caffeine identified according to the SELEX and counter-SELEX procedures. More specifically, this invention includes nucleic acid sequences that are substantially homologous to and that have substantially the same ability to bind caffeine as the specific nucleic acid ligands shown in FIG. 8. The present invention also includes nucleic acid ligands that have substantially the same structure as the ligands presented herein and that have substantially the same ability to bind caffeine as the nucleic acid ligands shown in FIG. 8.

The SELEX Patent Applications disclose modified nucleic acid ligands, wherein certain chemical modifications have been made in order to increase the in vivo stability of the ligand, enhance or mediate the delivery of the ligand, or reduce the clearance rate from the body. Examples of such modifications include chemical substitutions at the ribose and/or phosphate and/or base positions of a given RNA sequence. See, e.g., Cook et al. PCT Application WO 92/03568; U.S. Pat. No. 5,118,672 of Schinazi et al.; Hobbs et al. (1973) Biochem. 12:5138; Guschlbauer et al. (1977) Nucleic Acids Res. 4:1933; Schibaharu et al. (1987) Nucleic Acids Res. 15:4403; Pieken et al. (1991) Science 253:314, each of which is specifically incorporated herein by reference. SELEX may be performed with a starting candidate mixture of oligonucleotides containing modified nucleotides. Further, modified nucleotides may be incorporated into nucleic acid ligands identified by SELEX from oligonucleotides not containing modified nucleotides. The present invention includes modified nucleic acid ligands of theophylline and caffeine. Specifically included within the scope of this invention are RNA ligands of theophylline and caffeine that contain 2'-$NH_2$ and/or 2'-F modifications of certain riboses of the RNA ligand.

The nucleic acid ligands and nucleic acid ligand solutions to theophylline and caffeine described herein are useful as diagnostic reagents. Further, the nucleic acid ligands to theophylline and caffeine described herein may be used beneficially for therapeutic purposes.

The present invention shows how SELEX can be applied to generate oligonucleotides with binding and discriminatory properties for theophylline and caffeine superior in certain respects to those of monoclonal antibodies. As is shown below, SELEX selected nucleic acid ligands to theophylline have an affinity for theophylline comparable to that of monoclonal antibodies but with a superior selectivity.

The present invention includes a novel modification of the SELEX method, herein termed "counter-SELEX". The counter-SELEX method is a powerful means of eliminating undesired sequences from a SELEX experiment. The significance of this technique is that it provides a means for increased specificity of SELEX pools. Also it provides a methodology for decreasing the number of SELEX selection rounds required to identify a high affinity and high specificity nucleic acid ligand. Further, it provides a methodology for identifying a nucleic acid ligand of a target molecule that does not cross-react with other molecules, including closely related molecules.

Generally, the method of counter-SELEX is comprised of the steps of: a) preparing a candidate mixture of nucleic acids. The candidate mixture may contain nucleic acids with one or more types of modified nucleotides; b) contacting the candidate mixture with the target molecule. Nucleic acids having an increased affinity to the target relative to the candidate mixture will bind the target molecule and may be partitioned from the remainder of the candidate mixture. The target molecule may be but is not necessarily attached to a column; c) partitioning the increased affinity nucleic acids from the remainder of the candidate mixture; d) contacting the increased affinity nucleic acids with one or more non-target molecules such that nucleic acids bound to the target molecule with affinity to a non-target molecule are removed; and e) amplifying the nucleic acids with specific affinity to the target molecule to yield a mixture of nucleic acids enriched for sequences with a relatively higher affinity and specificity to the target molecule.

In one embodiment of the counter-SELEX method, counter-SELEX is conducted with oligonucleotides bound to a column. This embodiment is used to eliminate oligonucleotides with undesired cross-reactivities which bind the target molecule. Briefly, the target molecule is bound to a column, and a candidate mixture of oligonucleotides applied to the column such that oligonucleotides binding the target molecule are retained in the column. The column is then washed with the binding buffer to remove non-binding oligonucleotides. Then one or more non-target molecules, or counter-ligands, to which cross-reactivity is undesirable, are applied in solution to the column in vast molar excess. Molar excess may be defined as $10^3$–$10^4$ times the amount bound to the column. This results in the removal of bound oligonucleotides from the column which also bind the counter-ligand(s). The target molecule is then applied to the column in solution, in vast molar excess, to remove oligonucleotides with the desired ligand binding specificity. Counter-SELEX may be conducted with a single counter-ligand molecule, with sequential exposure to more than one counter-ligand, or with a cocktail of several related counter-ligands, to eliminate oligonucleotides with cross-reactivity to several compounds. Further, counter-SELEX may be conducted after pre-selection of oligonucleotides for affinity for a target molecule by one or more selection rounds of SELEX.

In a second embodiment of the counter-SELEX method, counter-SELEX is conducted in solution. This approach is designed to eliminate oligonucleotides with undesired cross-reactivity in solution. In this embodiment of counter-SELEX, the binding of oligonucleotides to a target on a column is performed with the counter-ligand present in the binding buffer. Once the oligonucleotides are bound to the target, the column is vigorously washed. This procedure prevents oligonucleotides with cross-reactivity to the counter-ligand from binding to the column. This embodiment of the counter-SELEX method may be used in SELEX experiments for binding to peptides with sequences related to other peptides. This embodiment is intended to eliminate possible side effects due to cross-reactivity of SELEX selected oligonucleotides with other target molecules in vivo. For example, SELEX may be performed to identify nucleic acid ligands to a peptide hormone such as vasointestinal peptide (VIP). The amino acid sequence of VIP is similar to that of the peptide hormone glucagon, which has several essential roles in vivo. With the second embodiment of counter-SELEX, nucleic acid ligands to VIP are identified which do not cross-react with glucagon in solution, and therefore, would not cross-react with glucagon in vivo. This embodiment of the counter-SELEX procedure may be performed with one or more counter-ligand molecules in solution to eliminate nucleic acid ligands with cross-reactivity to more than one target molecule in vivo. Further, counter-SELEX may be conducted after one or more selection rounds of SELEX.

The utility of the counter-SELEX procedure for accelerating the enrichment of the target molecule binding nucleic acid species is illustrated by comparing the binding properties of pooled RNA after an identical number of selection rounds of SELEX and counter-SELEX. After three SELEX selection rounds, 12% of RNA initially bound to immobilized theophylline was resistant to subsequent elution with caffeine (TR8). After three counter-SELEX selection rounds with caffeine, 45% of initially bound RNA was resistant to caffeine elution (TCT8).

DNA sequence analysis was carried out on double-stranded cDNA populations derived from the pools of the 8th selection round SELEX RNAs (TR8) (Example 1) and counter-SELEX (TCT8) (Example 2). This analysis revealed that both pools were decidedly non-random in sequence (data not shown). The cDNAs were inserted into plasmids and bacterial clones generated. From plasmid DNAs isolated from the bacterial clones, the relevant regions encoding the RNA ligands were amplified by PCR and their sequences determined. The sequence of eleven TCT8 and eight TR8 clones are shown in FIGS. 2A and 2B. The ligands selected to bind to theophylline show a remarkable 15 base sequence which is completely conserved at 14 positions and present in each TCT8 and TR8 clone. This sequence is comprised of two separate motifs: motif 1 is 5'-AUACCA-3' (SEQ ID NO:1) and motif 2 is 5'-CCU-UGG(C/A)AG-3' (SEQ ID NO:2). The sequences and spacing between motifs 1 and 2 are variable among the ligands, ranging from 8 to 20 residues.

Inspection of the sequences located between the motifs in the different ligands provides important information about the potential secondary structures of these RNAs. It is possible to fold all of the TCT8 and TR8 ligands into a similar generic secondary structural conformation, shown in FIG. 4. These conformations show the variable region and limited regions of the flanking fixed regions postulated to participate in the secondary structure. Several features of these conformations are notable. Specifically, each ligand contains two stems of variable length and sequence loop, termed "vstem1" and "vstem2" and a variable length and sequence loop, termed "vloop". These structural features flank the conserved motifs in the model. Motif 1 and 2 are based-paired through interaction of the CCA triplet of motif 2 with the UGG triplet of motif 1. In all cases, the CCU triplet of motif 1 is depicted as an asymmetric bulge. The model accommodates the remaining six nucleotides of the conserved region as a symmetric bulge consisting of the AUA of motif 2 opposed to (C/A)AG of motif 1. This bulge is closed by a stem of variable length and sequence. The relative spatial orientation of the CCU and (C/A)AG components is clearly specific in this family of ligands since their orientations are preserved whether the CCU component is located 3' (e.g., TCT8-5, TCT8-7, TCT8-8, TCT8-1, TCT8-6) or 5' (e.g., TCT8-11, TCT8-3). It is notable that closure of the symmetric bulge often involves participation of the fixed sequences, either from the 5' (e.g., TCT8-5) or 3' regions (e.g., TCT8-7). The conservation of the 15 nucleotides in each clone suggests that the remaining structural components of variable sequence such as vloop and vstems 1 and 2 do not play a direct role in binding theophylline. The vloop and vstems may play a structural role in positioning a binding surface or pocket comprised of the conserved bases. A consensus secondary model is depicted in FIG. 4.

The present invention shows that nucleic acids can interact specifically with a therapeutically important small molecule, further confirming the possible use of these oligonucleotides as diagnostic reagents. Currently, monoclonal antibodies are commonly used to determine serum theophylline levels (Poncelet et al. J. Immunoassay 11:77). The affinity of the RNA ligands for theophylline is comparable to that of the antibodies used in clinical assays (Poncelet et al. supra). Although these antibodies vary in their ability to discriminate amongst related compounds, typically they show 0.1–1% cross-reactivity with compounds such as caffeine and theobromine. The discrimination of the RNA ligands described here is at least an order of magnitude greater than such antibodies. These results help establish the fact that oligonucleotides can display unexpected recognition and specificity properties.

In addition to the work described here, the structural versatility of RNA is attested to by its ability to interact with other small molecules. These include the interaction of type I introns with guanosine (Bass and Cech (1984) Nature 308:820) and arginine (Yarus (1988) Science 240:1751), the binding of arginine by HIV TAR RNA (Tao and Frankel (1992) Proc. Natl. Acad. Sci. USA 89:2723), and the binding of a set of uncharacterized RNAs with amino-linked tryptophan agarose (Famulok and Szostak (1992) J. Amer. Chem. Soc. 114:3990). Of particular relevance to the work described here are the observations of stereoselective recognition by RNA of arginine (Yarus (1988) supra) and tryptophan (Famulok and Szostak (1992) supra). The detailed structure of the binding pockets of these ligands has been the subject of intense study. An important feature of the SELEX process is that it yields families of sequences whose similarities reveal important higher order structural clues. These clues provide starting points for modeling and analysis of structure by chemical and physical methods. In addition, the counter-SELEX procedure described herein may be used to accelerate the rate at which specific ligands are obtained, and more importantly, to selectively remove from the oligonucleotide population those species with affinity for targets that are structurally closely related to the target of interest. The present invention verifies the potential application of SELEX to include virtually any molecule of biomedical interest, irrespective of size and chemical class.

The following examples are explanatory and exemplary of the present invention. Example 1 describes the general experimental procedures used in the present work, including the equilibrium filtration analysis and the selection of the theophylline family of ligands TR8 after 8 rounds of selection of SELEX. Example 2 describes the selection of the theophylline ligand family TCT8, selected after 5 selection rounds of SELEX and 3 selection rounds of counter-SELEX with caffeine. Example 3 describes the identification of the caffeine ligand family CR8 after eight rounds of selection of SELEX. Example 4 describes the binding characteristics of a representative theophylline RNA ligand (TCT8-4). The results show that TCT8-4 bound theophylline with a Kd of 0.58 μM, similar to that observed for some monoclonal antibodies. A truncated ligand was constructed containing the conserved motif of TCT8-4 (mTCT8-4), and found to bind theophylline with a Kd of 0.11 μM, approximately 5.8-fold greater than the full-length ligand. Example 5 describes competition binding studies conducted with xanthine derivatives for RNA ligands for theophylline. These studies allow investigation of the relative contributions of various constituents to the overall binding. Example 6 describes aspects of molecular modeling of high affinity ligands for theophylline.

EXAMPLE 1

Experimental Procedures

Materials. 1-carboxypropyl theophylline was provided by Abbott Laboratories, Abbott Park, Ill.

SELEX. Essential features of the SELEX protocol have been described in detail in previous papers (Tuerk & Gold (1990) Science 249:505; Tuerk et al. (1992a) Proc. Natl.

Acad. Sci. USA 89:6988; Tuerk et al. (1992b) in Polymerase Chain Reaction (Ferre, F, Mullis, K., Gibbs, R. & Ross, A., eds.) Birkhauser, N.Y.). Briefly, DNA templates for in vitro transcription (that contain a region of forty random positions flanked by constant sequence regions) and the corresponding PCR primers were synthesized chemically (Operon). The random region was generated by utilizing an equimolar mixture of the four nucleotides during oligonucleotide synthesis. The two constant regions were designed to contain PCR primer annealing sites, a primer annealing site for cDNA synthesis, T7 RNA polymerase promoter region, and restriction enzyme sites that allow cloning into vectors.

Theophylline SELEX experiments utilized 100 mM HEPES buffer (100 mM HEPES, pH 7.3, 0.5M NaCl and 5 mM $MgCl_2$).

Cloning and Sequencing. Individual members of the enriched pools were cloned into $pUC_{18}$ vector and sequenced as described (Schneider et al. (1992) J. Mol. Biol. Proc. Natl. Acad. Sci. USA 89:6992; Tuerk & Gold (1990) supra).

Figure 5:
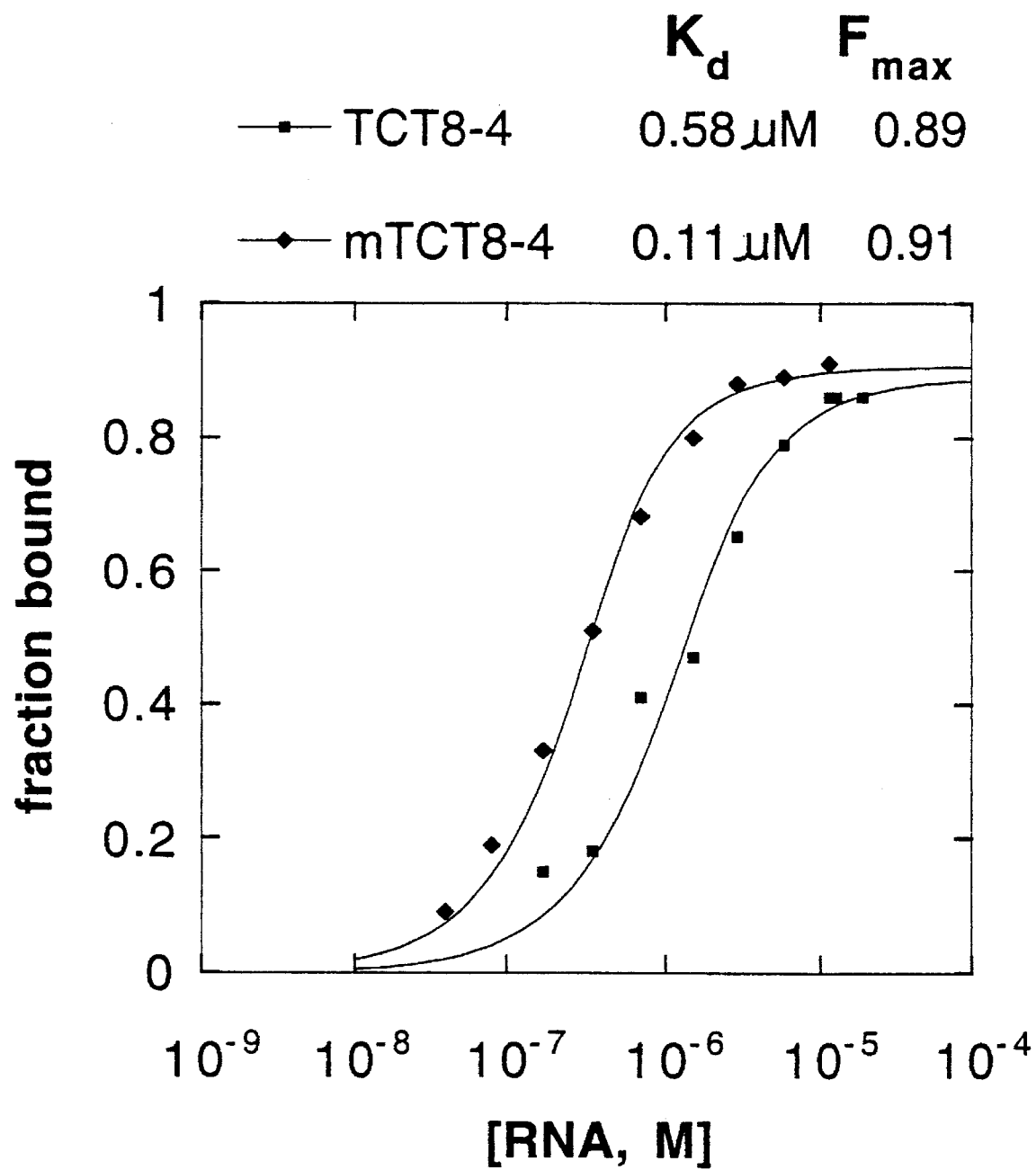
FIG. 5 shows the binding properties of TCT8-4 and mTCT8-4 RNAs.

Equilibrium filtration analysis. A rapid procedure was developed to assess theophylline binding by oligonucleotides, called "equilibrium filtration". These assays were performed by the addition of [$^{14}$C]-theophylline and RNA at the indicated concentrations (see FIG. 5) in a 150 µl reaction mixture containing 100 mM HEPES (pH 7.3), 5 mM $MgCl_2$ and 50 mM NaCl. Each binding mixture was incubated 5 min at 25° C. The mixture was then placed on a Microcon 10 (Amicon) filtration device and centrifuged 4 min at 14,000× g. Under these conditions, the RNA is retained by the filter while theophylline passes freely through the filter. A 25 µl sample was removed from each side of the filter and the radioactivity determined by scintillation counting. Each reaction was performed in triplicate. Other experiments established that this procedure provided results similar to that obtained by equilibrium dialysis. Equilibrium dialysis analysis of binding was carried out under identical reaction conditions to those described above. Each binding mixture was placed in a Spectra dialyzer (Spectrum) for 2 hr at 25° C. Radioactivity retained inside the chamber was determined. Data were fit by least squares to a quadratic binding equation assuming a 1:1 stoichiometry (Gill et al. (1991) J. Mol. Biol. 220:307 (FIG. 5).

Selection for RNA ligands to Theophylline. To screen for RNA molecules with affinity for theophylline, a pool of $10^{14}$ random RNAs were generated, each containing a 40 nucleotide random region flanked by fixed sequences for transcription and PCR amplification. These RNAs were generated by transcription of double-stranded DNA by T7 RNA polymerase as described above, and were radiolabelled with [α]$^{32}$P-ATP. The pool of labelled RNA was added to an EAH Sepharose column to which 1-carboxypropyl theophylline (1-cp theophylline) was covalently bound via an amide linkage using the coupling reagents 1-ethyl-3(3-dimethylaminopropyl carbodimide (EDC) and 60 N-hydroxysuccinimide (NHS). In each SELEX selection round, about 0.5 nmoles of RNA was added to columns containing about 50 nmoles of theophylline. The addition of 0.5M NaCl was found to be required to reduce non-specific RNA binding to the column. After allowing 10 min for interaction, the column was washed with loading buffer to remove non-specifically bound RNA. Bound RNA was partitioned by eluting with 0.1M theophylline. The eluted RNA was precipitated, reverse transcribed with AMV reverse transcriptase, and the resulting DNA amplified by PCR as described above. This set of procedures constituted one SELEX selection round.

Theophylline SELEX TR8. The general progress of the experiment over eight selection rounds was monitored by determining the percent of the labelled RNA input to each selection round that was specifically eluted from the theophylline column. About 0.05% of the random RNA in the first selection round was eluted from the column. After eight rounds of selection, approximately 62% of the input RNA was eluted by theophylline, representing an affinity enrichment of about 1200-fold, relative to the starting population. This SELEX experiment was designated TR8.

EXAMPLE 2

Counter-SELEX Selection for Theophylline Ligands: TCT8

A variation on the initial SELEX partition protocol was carried out after the fifth SELEX selection round. A different elution protocol was used to increase the stringency of the SELEX process. Rather than eluting with theophylline directly after washing, bound RNAs were first subjected to challenge with 0.1M caffeine after the fifth SELEX selection round. Remaining RNAs were eluted with 0.1M theophylline.

In the first counter-SELEX selection round, 99.7% of the theophylline-bound RNA was eluted with caffeine. The remaining 0.3% was eluted with theophylline and amplified. In the second counter-SELEX selection round, 70% of the bound RNAs were eluted with caffeine, the remaining 30% of bound RNAs were eluted with theophylline and amplified. A third and final counter-SELEX selection round generated a pool of RNAs termed "TCT8". Approximately 80% of the TCT8 RNAs bound directly to theophylline columns, representing an affinity enrichment of approximately 4000-fold relative to that of the starting population. Of the bound RNAs, 54% were resistant to caffeine challenge and were eluted subsequently by theophylline.

EXAMPLE 3

SELEX Selection for RNA Ligands to Caffeine

RNA ligands with high affinity to caffeine were identified in a similar fashion to the experiments described in Example 1. Eight selection rounds of SELEX were performed using Sepharose-bound caffeine as the molecular target. Bound RNAs were eluted with excess free caffeine. Enrichment of the populations of RNAs for those with affinity for caffeine proceeded similarly to the theophylline SELEX experiment. In the first selection round, about 0.01% of the random RNA was eluted with caffeine. After eight selection rounds, 52.5% of the input RNA was eluted with caffeine. Twenty-one bacterial clones were generated from this population, designated CR8 and sequenced as described in Example 1. CR8 sequences are shown in FIG. 8.

An important characteristic of the CR8 sequence family is that it lacks any apparent similarity to the 15 nucleotide conserved motifs of the theophylline RNA binding family (data not shown). Thus, surprisingly, RNAs selected for high affinity to caffeine are distinct from those selected to bind to theophylline. The binding properties of the CR8 RNA pool with $^{14}$C-caffeine were investigated by equilibrium dialysis. The CR8 RNA pool bound caffeine with a Kd of 15 µM, an affinity not dissimilar from that of the theophylline binding RNA population for theophylline after eight selection rounds.

EXAMPLE 4

Binding Characteristics of RNA Ligands for Theophylline

The binding properties of specific RNA species derived from the theophylline SELEX experiment were investigated by equilibrium filtration analysis with $^{14}$C-theophylline and varying concentrations of a representative SELEX ligand, TCT8-4. The results of these experiments indicated that the Kd of the TCT8-4 RNA-theophylline interaction was 0.58 µM (FIG. 5). This affinity is similar to that observed for some monoclonal antibodies raised against theophylline (Poncelet et al. (1990) supra).

Binding by Truncated RNA ligand to Theophylline (mTCT8-4). The hypothesis that the determinants in the TCT8-4 ligand responsible for high affinity binding to theophylline resided in the 15 nucleotide conserved domains was tested by determining the binding characteristics of a truncated RNA containing these domains and limited flanking residues. The mini-TCT8-4 RNA construct (mTCT8-4) (FIG. 6) is a 39 nucleotide T7 RNA polymerase transcript produced from a DNA template designed from the sequence of TCT8-4 RNA. The sequences of TCT8-4 present in mTCT8-4 are shown in FIG. 4. Essentially, mTCT8-4 contains motifs 1 and 2, and the 6 bp vstem1 and 4 bp vstem2 regions of TCT8-4. It lacks the 24 nucleotide 3' fixed region of the TCT8-4 RNA. mTCT8-4 RNA was produced by T7 RNA polymerase in vitro, gel purified, and tested for its ability to bind to $^{14}$C-theophylline by equilibrium filtration analysis. A Kd of 0.11 µM was determined for mTCT8-4 binding to theophylline (FIG. 5). This affinity is roughly seven-fold greater than that of TCT8-4, indicating that the presence of the flanking fixed sequence regions in TCT8-4 reduces affinity of the oligonucleotide, perhaps because of its influence on the conformation of the conserved sequence elements comprising the theophylline binding site. It is concluded that the structural determinants required for theophylline binding are entirely confined to the conserved regions of the oligonucleotide, whose specific three-dimensional orientation is likely dictated by non-conserved flanking stem and stem-loop domains.

EXAMPLE 5

Competition Binding Studies with Xanthine Derivatives

An attractive feature of a small molecule-RNA interaction is the opportunity to readily investigate quantitatively the relative contribution of various constituents of the small molecule to the overall binding. Competition binding experiments were conducted with a variety of xanthine derivatives and related compounds. In these experiments, the effect of competitor added at various concentrations on the $^{14}$C-theophylline-TCT8-4 RNA interaction was measured. Of particular interest were the roles of CH3 residues at the 1, 3, and 7 positions; these were assessed both individually and in combination. In addition, 1,3-dimethyluric acid probes the 8-position, as it contains a keto oxygen there relative to theophylline, and hypoxanthine, lacking the 2-position keto oxygen of xanthine, permit assessment of this constituent.

Figure 7:
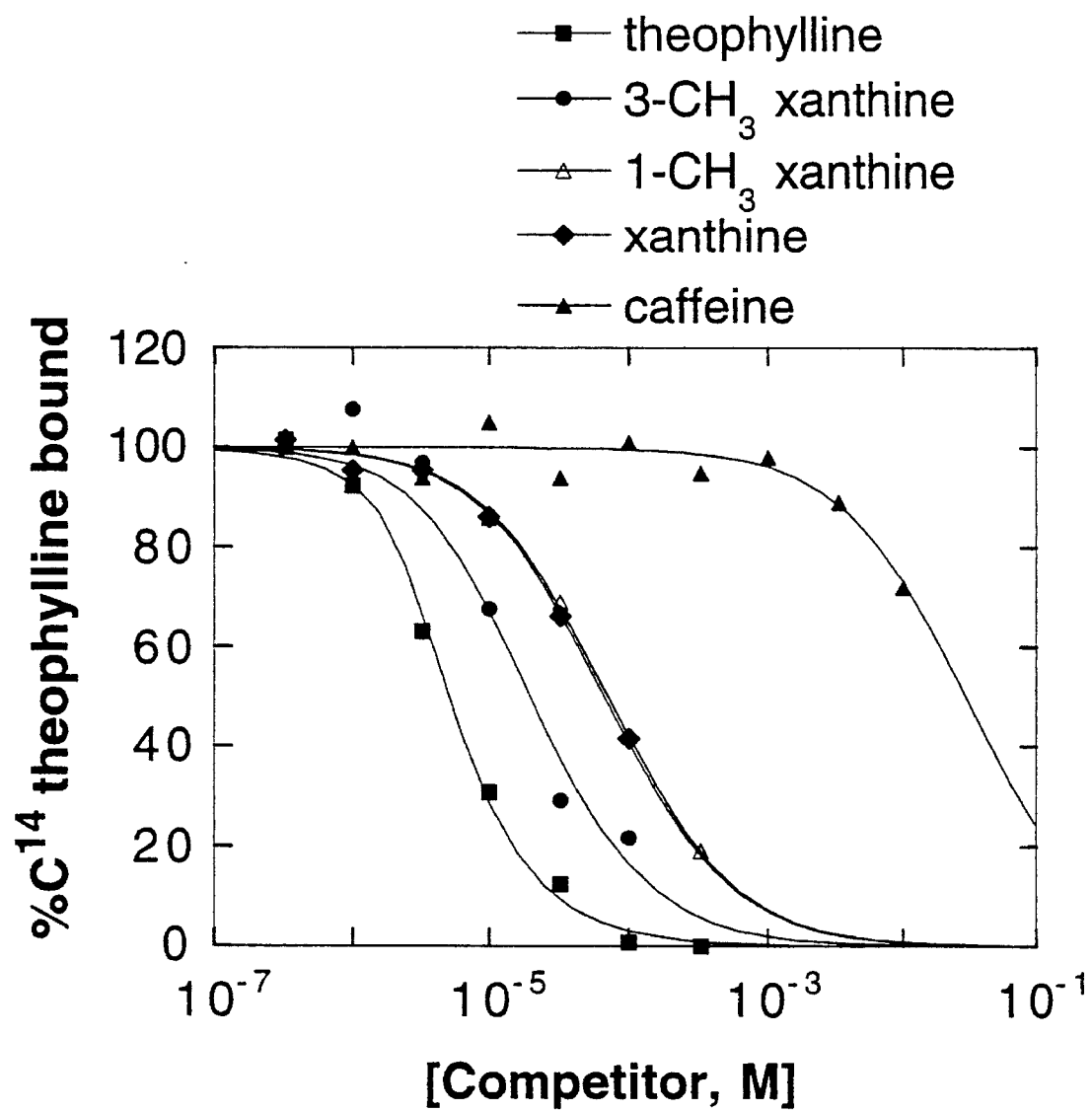
FIG. 7 shows the competition binding analysis of xanthine derivatives with TCT8-4 RNA.
Figure 9:
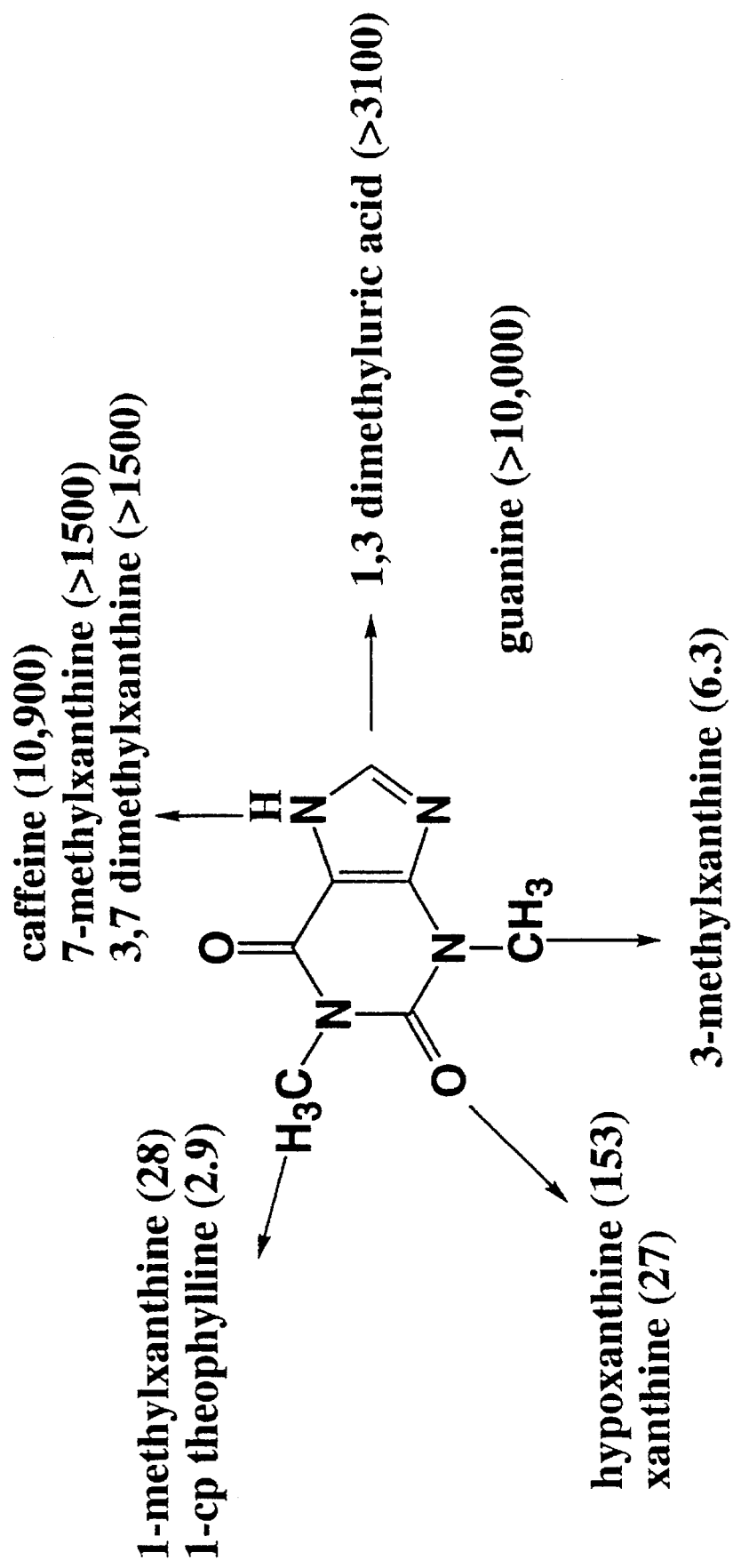
FIG. 9 illustrates the chemical structure of theophylline with a series of derivatives that were used in competitive binding experiments with TCT8-4 RNA as described in Example 5. The number in parenthesis represents the effectiveness of the competitor relative to theophylline, Kc(c)/Kc(t). Kc(c) is the individual competitor dissociation constant and Kc(t) is the competitive dissociation constant of theophylline. 1-cp theophylline is 1-carboxypropyl theophylline. Certain data, denoted by ">" are minimum values that were limited by solubility of the competitor. Each experiment was carried out in duplicate.

Equilibrium filtration assays were performed by the addition of various concentrations of the potential competitor to 1 µM [$^{14}$C]-theophylline and 3.3 µM TCT8-4 RNA in a 150 µl reaction mixture containing 100 mM HEPES buffer. Each reaction was performed as described in Example 1. Competition data were fit using a standard competition equation and fitting procedure (Gill et al. (1991) supra) assuming a 1:1 stoichiometry of competitor to RNA. A Kd=0.45 µM for theophylline to RNA was used. From such data a competitor dissociation constant (Kc) was obtained. Under the condition where theophylline and the specific competitor bind to the same site, Kc=Kd. These data are summarized in Table 1. Competition binding data are shown in FIG. 7.

TABLE 1

COMPETITION BINDING ANALYSIS WITH TCT8-4 RNA

| COMPETITOR | Kc (µM) | Kc(c)/Kc(t) |
|---|---|---|
| Theophylline | 0.32 ± 0.13 | 1 |
| CP-Theophylline | 0.93 ± 0.20 | 2.9 |
| Xanthine | 8.5 ± 0.40 | 27 |
| 1-methylxanthine | 9.0 ± 0.30 | 28 |
| 3-methylxanthine | 2.0 ± 0.7 | 6.3 |
| 7-methylxanthine | >500 | >1500 |
| 3,7-dimethylxanthine | >500 | >1500 |
| 1,3-dimethylxanthine | >1000 | >3100 |
| Hypoxanthine | 49 ± 10 | 153 |
| Caffeine | 3500 ± 1500 | 10900 |

Several features of the RNA binding surface are revealed by these studies. First, these results emphasize the major role played by the 7-position of xanthine derivative in recognition by the SELEX RNA. 7-methylxanthine competes at least 1500-fold less efficiently than xanthine, which itself is about 23-fold less effective than theophylline. The relatively good competition by xanthine indicates that the unadorned planar ring system is tightly accommodated by the RNA binding surface. As expected from the behavior of 7-methylxanthine, theobromine (3,7-dimethylxanthine) is also recognized poorly by TCT8-4 RNA. The 3-position provides positive binding energy as evidenced by the approximately 5-fold better competition of 3-methylxanthine relative to xanthine. In contrast, TCT8-4 RNA is relatively blind to the 1-position methyl, relative to xanthine. Hypoxanthine is bound about 5-fold more poorly by the RNA relative to xanthine, indicating that the 2-position keto oxygen is also important in the recognition. Finally, 1,3-dimethyl uric acid is very poorly recognized compared to theophylline, indicating that the binding site is highly sensitive to the 8-position.

Competition Binding studies with Caffeine.

Competition binding studies showed that caffeine is an extremely poor competitor of theophylline for RNA binding. The competition data are consistent with a Kd for caffeine of about 6.5 mM. Thus, TCT8-4 can discriminate between theophylline and caffeine at least 9000-fold, corresponding to a ΔG of about 5.6 kcal/mol. Relative to the truncated version of TCT8-4, mTCT8-4, the discrimination is approximately 60,000-fold. From these experiments, it is apparent that TCT8-4 RNA contains a binding surface or pocket that closely inspects the 7- and 8-positions of these xanthine derivatives, and discriminates between theophylline and caffeine largely on the basis of its inability to accommodate the 7-position methyl group of caffeine.

EXAMPLE 6

Molecular Modeling of High Affinity Ligand for Theophylline

The conserved sequences present in each of the class I and II molecules may be arranged in space in a way that ultimately rationalizes their high discrimination in recognizing theophylline. As an initial step, molecular modeling, energy minimization and molecular dynamics of the conserved region and flanking sequences were used to model a small oligonucleotide composed of the conserved sequences and limited flanking regions. This model incorporates A-form helical parameters derived from tRNA crystal data to model those portions predicted to be helical. Bulged nucleotides are believed to introduce local kinking into the helical axis (Riordan et al. (1992) J. Mol. Biol. 226:305). The three base pyrimidine bulge was modeled as stacked within the flanking helical regions based on similar tracts that have been analyzed in the HIV TAR RNA by NMR analysis (Puglisi et al. (1992) Science 257:76). In addition, preliminary nuclease mapping experiments indicate that the two C residues in this bulge are not accessible to nuclease CL3 (data not shown). The three base symmetric bulge was modeled using a central UA Watson-Crick base pair, flanked by two non-Watson-Crick CA base pairs, AC and AG. It is noteworthy that the single position of variability in the conserved sequences would allow CA or AA pairs, which are thought to be isosteric from artificial phylogeny experiments exploring RNA recognition of the HIV Rev Response Element by the Rev protein (Bartel et al. (1991) Cell 67:529; Ellington (1993) Current Biol. 3:375). Remarkably, in this model all of the conserved sequences play a coherent structural role in the formation of the major groove of the A-form helix that comprises the majority of the oligonucleotide. The asymmetric CCU bulge, and the non-Watson-Crick base pairs have the effect of slightly opening the major groove compared to that in fully duplex RNA. Such deformations of the major groove by helical perturbations provided by non-Watson-Crick pairs are a common theme of protein-RNA interactions (Bartel et al. (1991) supra; Ellington (1993) supra). While it is clear that theophylline can be physically accommodated in the major groove, the model lacks sufficient detail to rationalize the discrimination against caffeine binding (FIG. 7).

We claim:

1. A method for identifying nucleic acid ligands to a target molecule comprising:

a) preparing a candidate mixture of nucleic acids;

b) contacting the candidate mixture with the target molecule, wherein nucleic acids having an increased affinity to the target relative to the candidate mixture may be partitioned from the remainder of the candidate mixture;

c) partitioning the increased affinity nucleic acids from the remainder of the candidate mixture;

d) contacting the increased affinity nucleic acids with one or more non-target molecules, wherein nucleic acids with affinity to the non-target molecule(s) are removed; and e) amplifying the nucleic acids with specific affinity to the target molecule to yield a mixture of nucleic acids enriched for nucleic acid sequences with relatively higher affinity and specificity for binding to the target molecule, whereby nucleic acid ligands of the target molecule may be identified.

2. The method of claim 1 further comprising f) repeating steps b), c), d) and e).

3. The method of claim 1 wherein said target molecule is immobilized on a column.

4. The method of claim 1 wherein said candidate mixture of nucleic acids is comprised of single stranded nucleic acids.

5. A purified and isolated non-naturally occurring RNA ligand to theophylline, wherein the nucleotide sequence of said RNA ligand is selected from the group consisting of the nucleotide sequences set forth in FIGS. 2A and 2B (SEQ ID NOS: 3–15).

6. A purified and isolated non-naturally occurring RNA ligand to caffeine, identified by the method of claim 1, wherein the nucleotide sequence of said RNA ligand is selected from the group consisting of the nucleotide sequences set fourth in FIG. 8 (SEQ ID NOS:16–27).

7. Nucleic acid ligands to theophylline identified according to a method for identifying nucleic acid ligands from a candidate mixture comprised of nucleic acids, said method comprising:

a) preparing a candidate mixture of nucleic acids;

b) contacting said candidate mixture with theophylline, wherein nucleic acids having an increased affinity to theophylline relative to the candidate mixture may be partitioned from the remainder of the candidate mixture;

c) partitioning the increased affinity nucleic acid ligands from the remainder of the candidate mixture; and d) amplifying the increased affinity nucleic acids to yield a ligand-enriched mixture of nucleic acid, whereby nucleic acid ligands of theophylline may be identified.

8. The method of claim 7 further comprising e) repeating steps b), c) and d).

9. Nucleic acid ligands to caffeine identified according to a method for identifying nucleic acid ligands from a candidate mixture comprised of nucleic acids, said method comprising:

a) preparing a candidate mixture of nucleic acids;

b) contacting said candidate mixture with caffeine, wherein nucleic acids having an increased affinity to caffeine relative to the candidate mixture may be partitioned from the remainder of the candidate mixture;

c) partitioning the increased affinity nucleic acid ligands from the remainder of the candidate mixture; and d) amplifying the increased affinity nucleic acids to yield a ligand-enriched mixture of nucleic acid, whereby nucleic acid ligands of caffeine may be identified.

10. The method of claim 9 further comprising e) repeating steps b), c) and d).

11. The method of claim 1 wherein said target molecule is theophylline.

12. A nucleic acid ligand to theophylline, identified according to the method of claim 11.

13. The method of claim 1 wherein said target molecule is caffeine.

14. A nucleic acid ligand to caffeine identified according to the method of claim 13.

15. A non-naturally occurring nucleic acid ligand, having a specific binding affinity for a target molecule, wherein said nucleic acid ligand is not a nucleic acid having the known physiological function of being bound by the target molecule, and wherein said target molecule is selected from the group consisting of theophylline and caffeine.

16. A method for identifying nucleic acid ligands to a target molecule comprising:

(a) preparing a candidate mixture of nucleic acids;

(b) contacting the candidate mixture with one or more non-target molecules, wherein nucleic acids with affinity to the non-target molecule(s) are removed;

(c) contacting the candidate mixture from (b) with the target molecule, wherein nucleic acids having an increased affinity to the target relative to the candidate mixture may be partitioned from the remainder of the candidate mixture;

(d) partitioning the increased affinity nucleic acids from the remainder of the candidate mixture;

(e) amplifying the nucleic acids with specific affinity to the target molecule to yield a mixture of nucleic acids enriched for nucleic acid sequences with relatively higher affinity and specificity for binding to the target molecule, whereby nucleic acid ligands of the target molecule may be identified.

* * * * *

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

A U A C C A       6

( 2 ) INFORMATION FOR SEQ ID NO:2:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

C C U U G G M A G       9

( 2 ) INFORMATION FOR SEQ ID NO:3:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

G A G A A A U A C C   A G U G A C A A C U   C U C G A G A U C A   C C C U U G G A A G       4 0

( 2 ) INFORMATION FOR SEQ ID NO:4:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

AUACCAUCGU GUAAGCAAGA GCACGACCUU GGCAGUGUGU G 41

(2) INFORMATION FOR SEQ ID NO:5:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:5:

GAUACCAGCA GCAUAUUUGC UGUCCUUGGA AGCAACGAGA 40

(2) INFORMATION FOR SEQ ID NO:6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:6:

GUGAUACCAG CAUCGUCUUG AUGCCCUUGG CAGCACUUCA 40

(2) INFORMATION FOR SEQ ID NO:7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:7:

UUGUCGAAUC GGAUACCAGC AAUGCAGCCC UUGGAAGCAG 40

(2) INFORMATION FOR SEQ ID NO:8:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:8:

GAUACCAACG GCAUAUUUGC UGUCCUUGGA AGCAACUAUA 40

(2) INFORMATION FOR SEQ ID NO:9:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:9:

CUCUCGAAAU ACCAACUACU CUCACAAUAG UCCUUGGAAG 40

(2) INFORMATION FOR SEQ ID NO:10:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:10:

UUCAUGUCGC UUGAUACCAU CAACAAUGAC CUUGGAAGCA 40

( 2 ) INFORMATION FOR SEQ ID NO:11:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

UGACUCGAAC CCUUGGAAGA CCUGAGUACA GGUAUACCAG      40

( 2 ) INFORMATION FOR SEQ ID NO:12:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

UCCUUGGAAG CCGUACGGAU ACCAAUUGAG UGGCCAUAUG      40

( 2 ) INFORMATION FOR SEQ ID NO:13:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

UAUCGAGUGG CCUUGGCAGA CCAGGCCCGG UAUACCACCA      40

( 2 ) INFORMATION FOR SEQ ID NO:14:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CGAGAUUCAA CCUUGGAAGU CAAUCGUGAA UACCAUUGUU      40

( 2 ) INFORMATION FOR SEQ ID NO:15:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

UCAGAACCUU GGAAGCACUG AAUAAGAUCA GUUGAUACCA      40

( 2 ) INFORMATION FOR SEQ ID NO:16:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GGACGAGACT CATCGTAACC TAGATGGTTG CCAGCATTTA      40

( 2 ) INFORMATION FOR SEQ ID NO:17:

( i ) SEQUENCE CHARACTERISTICS:
     ( A ) LENGTH: 40 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:17:

GGATGCTTAC AGCATAATCG GAATTGATTG CCAGCGGAAA      40

( 2 ) INFORMATION FOR SEQ ID NO:18:

( i ) SEQUENCE CHARACTERISTICS:
     ( A ) LENGTH: 40 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:18:

GGGGCAATAG AAGCCAACGC ACAGTCGTTG CCAGTGTTCG      40

( 2 ) INFORMATION FOR SEQ ID NO:19:

( i ) SEQUENCE CHARACTERISTICS:
     ( A ) LENGTH: 40 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:19:

GGGATGGATC TTCGGATACG TCAACCAAAG GTTGCCAGCG      40

( 2 ) INFORMATION FOR SEQ ID NO:20:

( i ) SEQUENCE CHARACTERISTICS:
     ( A ) LENGTH: 40 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:20:

GCGCATCGTA AAAAGGACAA ACGTCGTCGT GACCCCGATA      40

( 2 ) INFORMATION FOR SEQ ID NO:21:

( i ) SEQUENCE CHARACTERISTICS:
     ( A ) LENGTH: 40 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:21:

GTGCATCGTA AAAAGGACAA ACGTCGTCGT GACCCCGATA      40

( 2 ) INFORMATION FOR SEQ ID NO:22:

( i ) SEQUENCE CHARACTERISTICS:
     ( A ) LENGTH: 40 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:22:

AGACGGTGAA ACTGAAATCT AATCCGTCTG AACCCTGGAT      40

( 2 ) INFORMATION FOR SEQ ID NO:23:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:23:

AGACGGTGAA GCTGAAATCT AATCCGTCTG AACCCTGGAC 40

( 2 ) INFORMATION FOR SEQ ID NO:24:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:24:

GGGAGGTCAA GGACCTCACA CTTTTGTGTG CCAGCGCTAT 40

( 2 ) INFORMATION FOR SEQ ID NO:25:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:25:

GAAAGCGTTG TGGCGTGCCA TCGCCCGCAG GCGAATAACA 40

( 2 ) INFORMATION FOR SEQ ID NO:26:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:26:

ACGATGGGTT GTTATAGTGG AAACGGTAAG TTCGAGTCTG 40

( 2 ) INFORMATION FOR SEQ ID NO:27:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:27:

ACGGTGATCC TCTAATCCGT CGACAGAATC GATGTCAATC 40

( 2 ) INFORMATION FOR SEQ ID NO:28:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:28:

AACGCUCAAU ACCAUCGUGU AAGAAAGAGC ACGACCUUGG CAGUGUGUGU 50
U 51

( 2 ) INFORMATION FOR SEQ ID NO:29:

( i ) SEQUENCE CHARACTERISTICS:
  ( A ) LENGTH: 42 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:29:

AAGUGAUACC AGCAUCGUCU UGAUGCCCUU GGCAGCACUU CA   42

( 2 ) INFORMATION FOR SEQ ID NO:30:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:30:

GAUACCAACA GCAUAUUUGC UGUCCUUGGA AGCAACGAGA   40

( 2 ) INFORMATION FOR SEQ ID NO:31:

( i ) SEQUENCE CHARACTERISTICS:
  ( A ) LENGTH: 42 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:31:

GAGAAAUACC AGUGACAACU CUCGAGAUCA CCCUUGGAAG UU   42

( 2 ) INFORMATION FOR SEQ ID NO:32:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:32:

UAUCGAGUGG CCUUGGCAGA CCAGGCCGGG UAUACCACCA   40

( 2 ) INFORMATION FOR SEQ ID NO:33:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:33:

CGAGAUUCAA CCUUGGAAGU CAAUCGUGAA UACCAUUGUU   40

( 2 ) INFORMATION FOR SEQ ID NO:34:

( i ) SEQUENCE CHARACTERISTICS:
  ( A ) LENGTH: 45 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:34:

UGACUCGAAC CCUUGGAAGA CCUGAGUACA GGUAUACCAG UUCGA   45

( 2 ) INFORMATION FOR SEQ ID NO:35:

( i ) SEQUENCE CHARACTERISTICS:
  ( A ) LENGTH: 47 base pairs (B) TYPE: nucleic acid
(C) STRANDEDNESS: single
(D) TOPOLOGY: linear (xi) SEQUENCE DESCRIPTION: SEQ ID NO:35:

CGCUCAAUCC UUGGAAGCCG UACGGAUACC AAUUGAGUGG CCAUAUG          47

(2) INFORMATION FOR SEQ ID NO:36:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:36:

NNAUACCANN NNNNNNCCU UGGMAGNN          28

(2) INFORMATION FOR SEQ ID NO:37:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:37:

GGUGAUACCA GCAUCGUCUU GAUGCCCUUG GCAGCACC          38